(12) United States Patent
Webb

(10) Patent No.: US 9,408,570 B2
(45) Date of Patent: Aug. 9, 2016

(54) PHYSIOLOGICAL FEATURE EXTRACTION AND FUSION TO ASSIST IN THE DIAGNOSIS OF POST-TRAUMATIC STRESS DISORDER

(71) Applicant: The Charles Stark Draper Laboratory, Inc., Cambridge, MA (US)

(72) Inventor: Andrea K. Webb, Medford, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 205 days.

(21) Appl. No.: 14/267,281

(22) Filed: May 1, 2014

(65) Prior Publication Data

US 2014/0330089 A1   Nov. 6, 2014

Related U.S. Application Data

(60) Provisional application No. 61/819,095, filed on May 3, 2013.

(51) Int. Cl.
| | | |
|---|---|---|
| *A61B 5/16* | (2006.01) | |
| *A61B 5/024* | (2006.01) | |
| *A61B 5/053* | (2006.01) | |
| *A61B 5/00* | (2006.01) | |

(52) U.S. Cl.
CPC ............ *A61B 5/165* (2013.01); *A61B 5/02405* (2013.01); *A61B 5/0531* (2013.01); *A61B 5/4884* (2013.01)

(58) Field of Classification Search
CPC ... A61B 5/165; A61B 5/02405; A61B 5/0531
See application file for complete search history.

(56) References Cited

U.S. PATENT DOCUMENTS

| | | | | |
|---|---|---|---|---|
| 8,622,901 | B2* | 1/2014 | Jain | A61B 5/0022 600/300 |
| 2009/0069641 | A1 | 3/2009 | Cho et al. | |
| 2010/0010371 | A1* | 1/2010 | Zayfert | A61B 5/16 600/558 |
| 2010/0036280 | A1* | 2/2010 | Ballegaard | A61B 5/4035 600/552 |
| 2010/0217098 | A1* | 8/2010 | LeBoeuf | A61B 5/00 600/301 |
| 2010/0249628 | A1* | 9/2010 | Kortelainen | A61B 5/1102 600/527 |

(Continued)

FOREIGN PATENT DOCUMENTS

WO    WO-2007/123923 A2    11/2007

OTHER PUBLICATIONS

International Search Report and Written Opinion mailed Aug. 18, 2014 in PCT Application No. PCT/US2014/036546 (10 pages).
Orr, et al., "Psychological assessment: clinical applications for PTSD." Journal of Affective Disorders 61 (2000) 225-240.
Orr, S., et. al, "Chapter 11: Physchophoysiological Assessment of PTSD." Assessing psychological trauma and PTSD. Ed. Wilson, J., et al. Guilford press, 2004.

(Continued)

*Primary Examiner* — Catherine Voorhees
(74) *Attorney, Agent, or Firm* — Edward A. Gordon; Paul S. Hunter; Foley & Lardner LLP

(57) ABSTRACT

Post-traumatic stress disorder (PTSD), and other anxiety disorders, are diagnosed via clinical interviews in which subjective self-reports of traumatic events and associated experiences are discussed with a mental health professional. The system and methods described herein classify and diagnose patients as suffering from anxiety disorders by measuring objective physiological measures, such as inter-heartbeat interval and skin conductance. The system measures various physiological measures and then extracts features from the physiological measures. A diagnosis is then made by classifying the extracted features using one of a neural network, Bayesian network, or a support vector machine.

18 Claims, 3 Drawing Sheets

(56) References Cited

U.S. PATENT DOCUMENTS

| | | |
|---|---|---|
| 2011/0066005 A1 | 3/2011 | Rotenberg |
| 2011/0191350 A1* | 8/2011 | Zhang .................... A61B 5/048 707/743 |
| 2013/0030241 A1 | 1/2013 | Smith |

OTHER PUBLICATIONS

Orr, Scott P. "Psychophysiologic Reactivity to Trauma-Related Imagery in PTSD." Annals of the New York academy of sciences 821, No. 1 (1997): 114-124.

* cited by examiner

PHYSIOLOGICAL FEATURE EXTRACTION AND FUSION TO ASSIST IN THE DIAGNOSIS OF POST-TRAUMATIC STRESS DISORDER

CROSS-REFERENCE TO RELATED APPLICATIONS

This application claims priority to U.S. Provisional Patent Application No. 61/819,095, filed May 3, 2013 and titled "PHYSIOLOGICAL FEATURE EXTRACTION AND FUSION TO ASSIST IN THE DIAGNOSIS OF POST-TRAUMATIC STRESS DISORDER," which is incorporated herein by reference in its entirety.

BACKGROUND

Post-traumatic stress disorder (PTSD) currently is diagnosed via subjective reports of experiences related to the traumatic event. More objective measures are needed to assist clinicians in diagnosis.

SUMMARY

According to one aspect of the disclosure, a method for diagnosing psychological trauma includes exposing a subject to a stimulus and collecting, with a plurality of sensors, a plurality of physiological signals. The physiological signals are collected during the subject's exposure to the stimulus. The plurality of physiological signals includes at least an interbeat interval signal and a skin conductance signal. The method also includes extracting a feature from each of the plurality of physiological signals, and classifying the subject into one of a plurality of diagnostic categories based on a function of the extracted features.

In some implementations, a first category of the plurality of diagnostic categories indicates the subject is suffering from post-traumatic stress disorder, a second category of the plurality of diagnostic categories indicates the subject is not suffering from post-traumatic stress disorder, and a third category of the plurality of diagnostic categories indicates the subject was exposed to a traumatic event but does not suffer from post-traumatic stress disorder.

In certain implementations, the extracted features include at least one of an area to full recovery, an area to half recovery, a peak amplitude, a standard deviation, a rise time from a first low point, a rise time from a response onset, a rise rate from a first low point, and an average value. In some implementations, the physiological signals includes at least one of a respiratory rate signal, a finger pulse amplitude signal, an electrocardiographic signal, an electrodermal activity (or skin conductance) signal, and an electroencephalographic signal.

In some implementations, the stimuli include at least one of audio stimulus and visual stimulus. In some implementations, the stimuli are presented to the subject via a virtual reality display device. The method can also include selecting the stimuli based on a traumatic event previously experienced by the subject.

In certain implementations, classifying the subject includes applying weights to the extracted features, combining the weighted features, and comparing the combined weighted features to a threshold. The threshold can be selected responsive to a baseline response of the subject and demographic characteristics of the subject, including, for example, at least one of an age of the subject, an ethnic background of the subject, and a sex of the subject.

In some implementations, the classification of whether the subject is suffering from post-traumatic stress disorder is made with one of a neural network, a Bayesian network, a linear discriminant classifier, or a support vector machine.

According to another aspect of the disclosure, a system for diagnosing psychological trauma includes an analog to digital converter (ADC). The ADC is configured to record a plurality of physiological signals during a subject's exposure to a stimulus. The plurality of physiological signals includes at least an interbeat interval signal and a skin conductance signal. The system also includes a feature extraction module configured to extract a feature from each of the plurality of physiological signals. The system further includes a classification module configured to classify the subject into one of a plurality of diagnostic categories based on a function of the extracted features.

In some implementations, a first category of the plurality of diagnostic categories indicates the subject is suffering from post-traumatic stress disorder, a second category of the plurality of diagnostic categories indicates the subject is not suffering from post-traumatic stress disorder, and a third category of the plurality of diagnostic categories indicates the subject was exposed to a traumatic event but does not suffer from post-traumatic stress disorder.

In some implementations, the system includes a stimulus delivery system. The stimulus delivery system is configured to expose the subject to a plurality of audio and/or visual stimuli. In certain implementations, the stimulus delivery system includes a virtual reality display and maybe configured to select the presented stimulus based on a traumatic event previously experienced by the subject.

In certain implementations, the classification module is configured to classify the subject using at least one of a neural network, a Bayesian network, a linear discriminant classifier, or a support vector machine. In some implementations, the classification module is configured to classify the subject by applying weights to the extracted features, combining the weighted features, and comparing the combined weighted features to a threshold. The threshold maybe selected responsive to at least one of an age of the subject, an ethnic background of the subject, a sex of the subject, and a baseline response of the subject.

In some implementations, the extracted physiological features includes at least one of an area to full recovery, an area to half recovery, a peak amplitude, a standard deviation, a rise time from a first low point, a rise time from a response onset, a rise rate from a first low point, and an average value.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Post-traumatic stress disorder (PTSD), and other mental health disorders such as depression and anxiety disorders, are typically diagnosed via clinical interviews in which subjective self-reports of traumatic events and associated experiences are discussed with a mental health professional. The system and methods described herein classify and diagnose patients as suffering from anxiety disorders by measuring objective physiological measures, such as inter-heartbeat interval and skin conductance.

Figure 1:
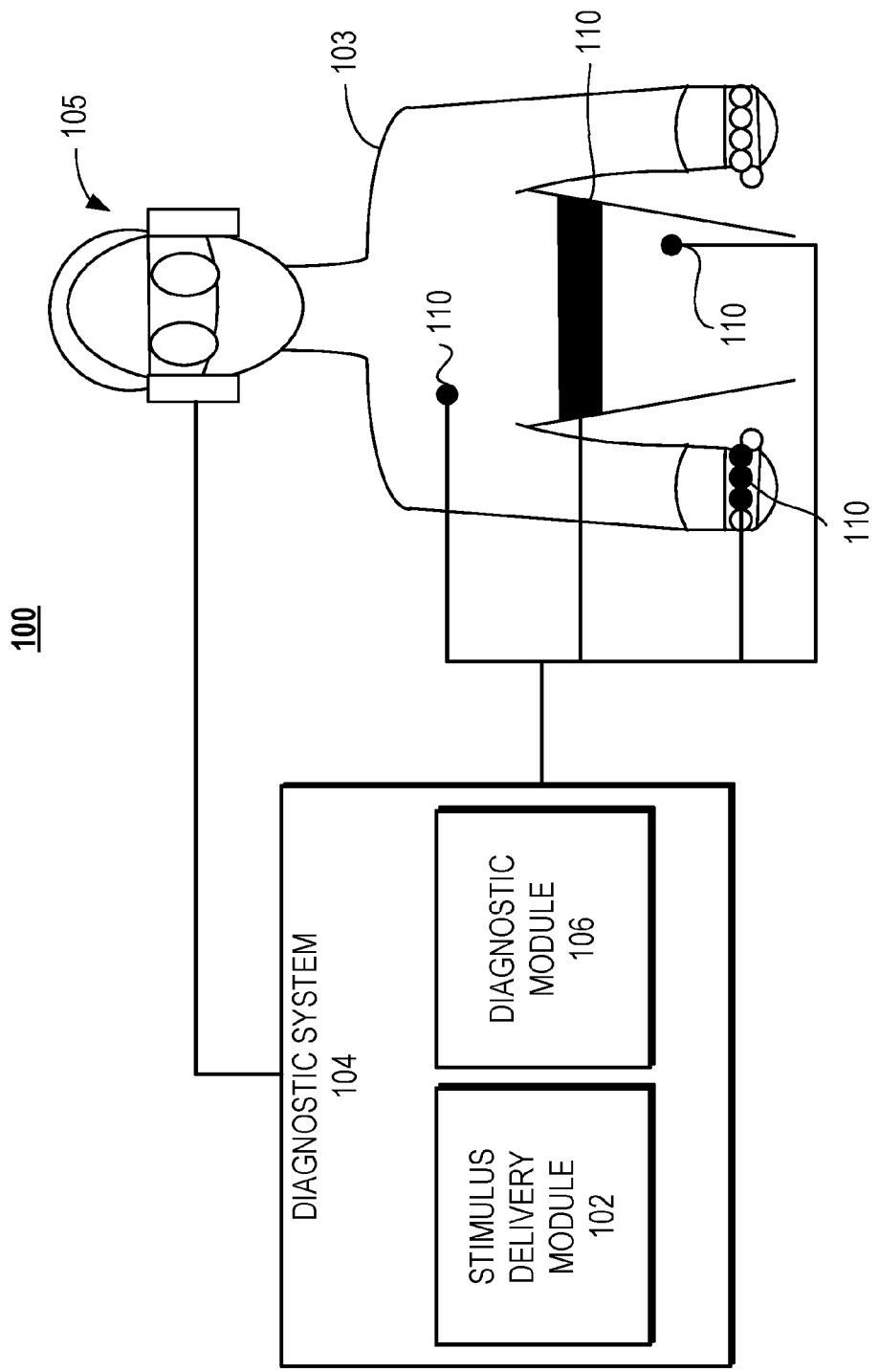
FIG. 1 illustrates a block diagram of an example system for diagnosing psychological trauma.

FIG. 1 illustrates a schematic diagram of an example system 100 for diagnosing psychological trauma. The system 100 includes a diagnostic system 104, which includes a stimulus delivery module 102 and a diagnostic module 106. The stimulus delivery module 102 provides audio and visual stimulus to the subject 103 through an immersive multimedia system 105. The diagnostic system 104 records physiological data from the subject 103 using a plurality of sensors 110.

The system 100 includes a diagnostic system 104. The diagnostic system 104 is discussed further in relation to FIG. 2. Briefly, the diagnostic system 104 collects one or more physiological signals from the subject 103. In some implementations, the physiological signals includes electrocardiographic data (e.g., heart rate and inter-heartbeat interval data), skin conductance data, finger pulse amplitude data, respiratory data (e.g., respiratory rate data), or any combination thereof. The diagnostic module 106 extracts features from the physiological signals. The diagnostic module 106 diagnoses the subject 103 by classifying the one or more physiological signals using one or more of the extracted features. In some implementations, the subject 103 is classified into a first category that indicates the subject is suffering from post-traumatic stress disorder, a second category that indicates the subject is not suffering from post-traumatic stress disorder, and a third category that indicates the subject was exposed to a traumatic event but does not suffer from post-traumatic stress disorder.

The diagnostic system 104 of the system 100 also includes a stimulus delivery module 102. The stimulus delivery module 102 delivers audio and visual stimulus to the subject 103 through the immersive multimedia system 105. As described below, the stimulus delivery module 102 includes a database of events. The events include visual and auditory stimulus related to different traumatic and non-traumatic events. For example, the stimulus delivery module 102 may include video clips representing the sounds and images of a battlefield (traumatic) and the sounds and images of a park (non-traumatic). In some implementations, the diagnostic system 104 is coupled to a network interface configured for wired or wireless data communications, and the processor outputs the results of the classification to a remote computing system over a computer network.

The system 100 also includes an immersive multimedia system 105. The stimulus delivery module 102, through the immersive multimedia system 105, delivers the audio and visual stimulus to the subject 103. For example, and as described below in relation to FIG. 2, when attempting to diagnose PTSD in a soldier, the stimulus delivery module 102 may expose the solider to a video of a road side bomb. In some implementations, the immersive multimedia system 105 includes a pair of virtual reality ("VR") goggles and a pair of headphones that are worn by the subject 103 during the diagnostic session. In some implementations, the VR goggles are 3D VR goggles with high definition, 1080p resolution or higher to provide a realistic visual environment to the subject 103. For example, in one implementation, the VR goggles can be the Z800 3D visor offered by eMagin of Bellevue, Wash. or the Oculus Rift virtual reality system by Oculus VR of Irvine, Calif. In some implementations, the immersive multimedia system 105 includes monitors, TV screens, flat panel displays, video walls, or any other type of display device to display the visual stimulus to the subject 103. In some implementations, the immersive multimedia system 105 presents auditory stimulus to the subject 103 through speakers.

The system 100 also includes a plurality of sensors 110. The sensors 110 record a plurality of physiological signals from the subject 103 in response to the subject's exposure to stimuli output by the stimulus delivery module 102. In some implementations, the sensors 110 are configured to monitor and record a plurality of different physiological responses, such as, but not limited to, respiration rate, heart rate, and skin conductance. For example, the sensors 110 can include EKG electrodes to measure heart rate and inter-heartbeat interval; a pneumography sensor coupled around the subject's chest to measure breathing rate; Ag—AgCl (or other electrode types) placed on the hands of the subject to measure skin conductance, light-emitting diodes (LEDS) coupled to the fingers of the subject 103 to measure pulse oximetry, finger pulse amplitude or pulse rate; or any combination thereof.

Figure 2:
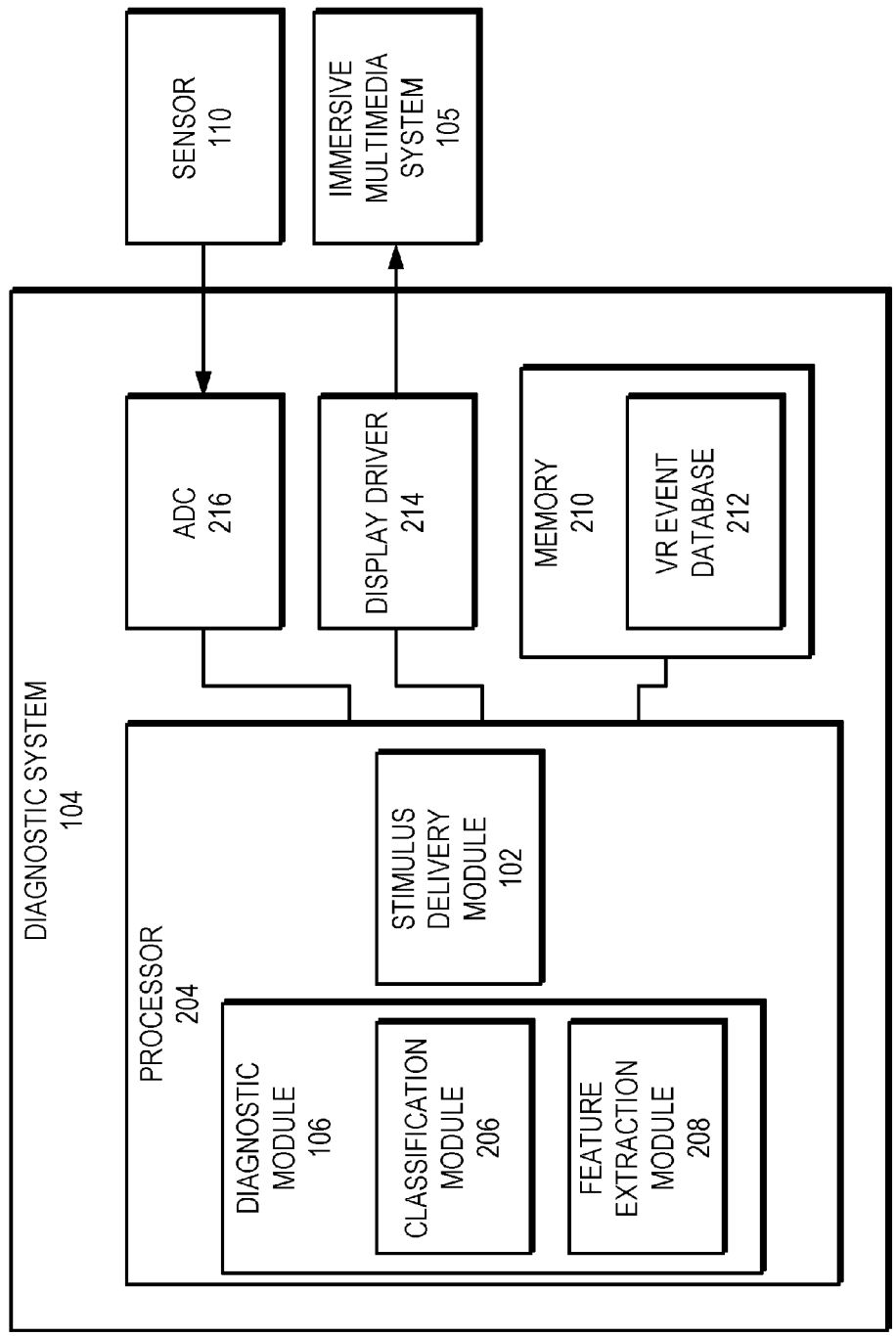
FIG. 2 illustrates a block diagram of the example diagnostic system from FIG. 1.

FIG. 2 illustrates a block diagram of the diagnostic system 104. The diagnostic system 104 includes a processor 204. The processor 204 includes the diagnostic module 106 and the stimulus delivery module 102. The diagnostic module 106 includes a classification module 206 and a feature extraction module 208. The diagnostic system 104 also includes memory 210 where a VR event database 212 is stored. The diagnostic system 104 also includes a display driver 214 to drive the immersive multimedia system 105. The diagnostic system 104 also includes an analog-to-digital converter (ADC) 216 to receive data from the sensors 110.

The diagnostic system 104 includes the processor 204. The processor 204 can be a general purpose processor executing computer executable instructions, which when executed carry out the functionality described herein. In other implementations, the processor 204 can be or can include a special purpose circuitry such as an application-specific integrated circuit (ASIC) or a field-programmable gate array (FPGA), configured specifically for carrying out the functionality described herein. In some implementations, the modules of the processor 204 are processor executable instructions stored in the memory 210 and executed by the processor 204.

The processor 204 of the diagnostic system 104 includes a diagnostic module 106. The diagnostic module 106, as described above, classifies the signals received from the sensors 110 to diagnose the subject 103. The diagnostic module 106 includes a feature extraction module 208. The feature extraction module 208 extracts features (or characteristics) from the physiological signals received from the sensors 110. In some implementations, the features include, without limitation, an area under the curve (of the signal) from response to full recovery, an area under the curve from response to half recovery, a peak amplitude, a standard deviation, a rise time from a first low point, a rise time from a response onset, a rise rate from a first low point, and an average value. In some implementations, different features are extracted from each of the different physiological signals. In some implementations, multiple features are extracted from one or more of the physiological signals. For example, the standard deviation and an area under the curve from response to full recovery may be extracted for inter-beat interval. The recovery time features represent the amount of time it takes for the subject's physiological characteristic, for example, respiration or skin conductance, to return to a baseline level after the subject 103 has been exposed to a stimulus corresponding to a traumatic event. Similarly, features related to an "onset" correspond to times from when a physiological characteristic is determined to have changed as a result of such a stimulus. Features that are a characteristic of the signal itself, such as standard deviation, are computed across all the samples in the signal (e.g., the standard deviation of the samples that make up the signal) or are windowed to determine how the characteristic changes over time (e.g., the standard deviation of the samples within each of a plurality of 1 second windows are compared to one another).

The diagnostic system 104 also includes a classification module 206. The classification module 206 receives the extracted features from the feature extraction module 208 and classifies the features as belonging to different diagnostic categories. In some implementations, the classification module 206 applies weights to the extracted features, combines the weighted features, and compares the combined value to a threshold to determine the classification of the subject 103. The weighted features can be combined by adding them together, multiplying them together, combining them according to a polynomial expression, or any other arithmetic process. In such implementations, the classification module 206 identifies the subject 103 as having PTSD if the combined value exceeds a threshold, and not having PTSD if the combined value falls below the threshold. In some implementations, the threshold is selected responsive to demographic characteristics of the subject, including one or more of the subject's age, ethnicity, and sex, and/or baseline recordings for the subject. In some implementations, the classification module 206 outputs a likelihood value corresponding to the determined classification. For example, the classification module 206 may output that there is a 96% chance that subject A suffers from post-traumatic stress disorder and a 21% chance that subject B suffers from post-traumatic stress disorder. In this example, based on the data input into the classification module 206, the classification module is 96% confident that subject A suffers from PTSD and 21% confident that subject B suffers from PTSD. In some implementations, the classification module 206 includes a neural network, a Bayesian network, a linear discriminant classifier, or a support vector machine to classify the extracted signals. The classification module 206 is trained on a training set of physiological feature data collected from a sufficiently large number of PTSD and non-PTSD sufferers to accurately output either a diagnosis or a likelihood value of the subject 103 suffering from PTSD.

The diagnostic system 104 also includes a stimulus delivery module 102. The stimulus delivery module 102 provides audio and visual stimulus to the display driver 214 for display to the subject 103 by the immersive multimedia system 105. In some implementations, the stimulus delivery module 102 selects traumatic and non-traumatic stimulus from the VR event database 212 to present to the subject 103. In some implementations, the display of traumatic and non-traumatic stimulus to the subject 103 is randomized. In some implementations, the stimulus delivery module 102 is configured to present a traumatic stimulus to the subject 103 and then present a non-traumatic stimulus to the subject 103 until the subject's physiological signals return to baseline (as determined by the diagnostic module 106). In some implementations, the stimulus delivery module 102 exposes the subject 103 to a baseline set of stimuli (e.g., non-traumatic) at the outset of an evaluation period to determine a baseline for each of the physiological signals, followed by a series of stimuli associated with one or more traumatic events. Suitable baseline stimuli may be imagery and audio corresponding to a substantially peaceful environment, such as the mountains, a beach, or other pastoral setting. In some other implementations, the baseline stimuli can correspond to imagery and audio associated with a typical living environment of the subject 103. For example, for city dwellers, such baseline stimuli may mimic a typical urban scene with standard traffic patterns and noises, whereas farm dwellers may be exposed to the sounds and scenes typical of a farm.

In some implementations, the traumatic stimulus is associated with a traumatic event, and in some implementations a specific traumatic event experienced by the subject 103. For example, the stimulus delivery module 102 may select a stimulus from the VR event database 212 that includes sounds of screams, gunshots, explosions, and/or vehicle collisions or crashes. Simultaneously, the stimulus delivery module 102 causes the stimulus delivery module 102 to display imagery that directly corresponds to the audio being presented to the subject 103. For example, the stimulus delivery module 102 may cause the stimulus delivery module 102 to display imagery corresponding to a firefight, to a car crash, an IED explosion, or other traumatic video. In other implementations, the stimulus delivery module 102 presents video imagery that may not necessarily correspond to the audio, to determine whether the audio itself may elicit a physiological response. For example, the stimulus delivery module 102 may, as a stimulus, present a scene of normal urban traffic coupled with the output of a "bang," which corresponds to a car back-firing, or in the mind of a sufferer of PTSD, a gunshot or other traumatic event.

Still referring to FIG. 2, the diagnostic system 104 also includes a display driver 214. As described above, the stimulus delivery module 102 delivers the stimulus to the subject 103 through the immersive multimedia system 105 via the display driver 214. In some implementations, the display driver 214 is a video card or other video output device. In some implementations, the display driver 214 includes a plurality of output ports to which the immersive multimedia system 105 is coupled. The ports can include, but are not limited to, HDMI, VGA, DVI, and DisplayPort ports. In some implementations, the display driver 214 is coupled to the immersive multimedia system 105 for presenting stimulus to the subject 103 and also to a monitor (or other display device) for displaying results to a physician, care provider, or other user of the system 100.

The diagnostic system 104 also includes an ADC 216. The ADC 216 receives sensor data from the plurality of the sensors 110 coupled to the subject 103. In some implementations, the ADC 216 includes a plurality of inputs to simultaneously receive data from each of the plurality of sensors 110 coupled to the subject 103. The ADC 216 has a resolution of 8, 12, 16, 32, 64, or more bits. In some implementations, the ADC 216 is external to the diagnostic system 104. For example, the ADC 216 may be a component of a standalone data acquisition system that receives data from the plurality of sensors 110 and then supplies the data in a digital format to the diagnostic system 104 through a USB, optical, or other digital connection. For example, the ADC 216 may be a component of a BIOPAC or National Instruments data acquisition system. In other implementations, the ADC 216 records and saves the sensor data from the sensors 110. The data is later provided to the diagnostic system 104 for "off-line" analysis at a time after the recording of the data. In some implementations, the ADC 216 may sample the data at about 128 Hz, at about 256 Hz, at about 512 Hz, at about 1024 Hz, at about 2024 Hz, or a higher sampling rate (for example at about the Nyquist rate of the signal being digitized). In some implementations, the ADC 216 is configured to digitize the signals received at each of its ports at different sampling rates responsive to the Nyquist rate of each of the signals. For example, respiration rate (with a relatively low Nyquist rate) may be recorded at a lower frequency that heart rate (with a relatively higher Nyquist rate). In some implementations, the ADC 216 filters the data (e.g., with a low pass or notch filter) to remove noise (or other artifacts) from the signals coming from the sensors 110.

Figure 3:
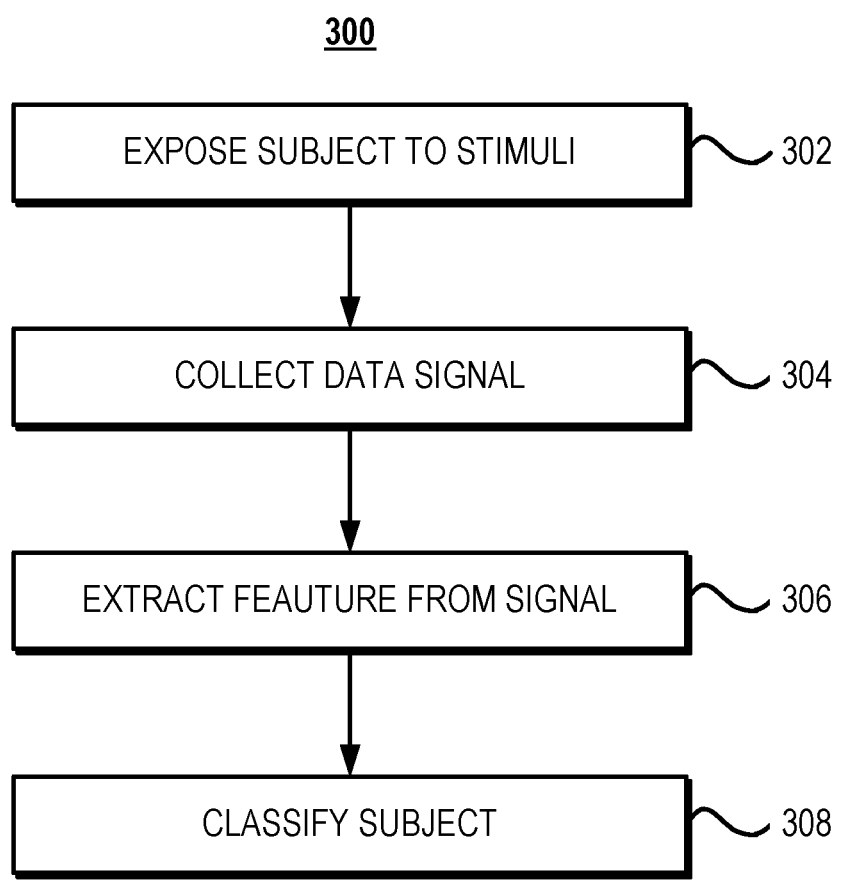
FIG. 3 illustrates a flow diagram of an example method for diagnosing psychological trauma in a subject using the system illustrated in FIG. 1.

FIG. 3 illustrates a flow chart of an example method 300 for diagnosing psychological trauma in a subject. The method 300 includes exposing the subject to stimuli (step 302). Physiological signals are collected from the subject with a plurality of sensors (step 304). Features are then extracted from the physiological signals (step 306). The subject is then classified responsive to the extracted features (step 308).

As set forth above, and referring to FIGS. 1 and 2, the method 300 includes exposing the subject to stimuli (step 302). Prior to exposing the subject to the stimuli, a plurality of sensors is coupled to the subject to collect physiological signals. After coupling the monitoring equipment (e.g., sensors) to the subject, the subject is exposed to the stimuli. In some implementations, the stimuli begin with a baseline, non-traumatic stimuli. After the baseline period, the diagnostic system 104 presents traumatic stimuli to the subject 103. For example, a video may include a Humvee driving scene. The scene begins and continues in a peaceful manner for approximately 30, 75, 120, 165, and 210 seconds to establish a baseline recording. Then different stimuli are presented to the subject 103 at different intervals. For example, the stimuli may include an aircraft flying overhead, a mortar explosion, an improvised explosive device (IED), an attack resulting in an explosion, and an attack by an insurgent.

As the subject 103 is exposed to the stimuli, one or more physiological signals are collected from the subject 103 with one or more sensors (step 304). As described above, the sensors collect, among others data types, respiration data, electrocardiogram data, electroencephalography data, pulse oximetry (including finger pulse amplitude) data, and electrodermal (e.g., skin conductance) data. The sensors are used as inputs to the ADC 216 of the diagnostic system 104. The ADC 216 conditions the collected signals for analysis and classification by the diagnostic module 106. For example, conditioning the signal can include filtering the signal to remove noise or amplifying the signal. In some implementations, the signals are collected and passed directly to the diagnostic module 106 for classification. In other implementations, the signals are stored in the memory 210 of the diagnostic system 104 for later analysis.

Features are then extracted from the collected signals (step 306). Examples of suitable features, include, without limitation, an area to full recovery, an area to half recovery feature, a peak amplitude, a standard deviation, a rise time from a first low point, a rise time from a response onset, a rise rate from a first low point, a time to full recovery of the signal (e.g., time to return to baseline), a latency time (e.g., the time between the presentation of the stimulus and the beginning of a change in the signal), and an average value. The features can be extracted for each physiological characteristic monitored by the sensors 110. For example, the feature extraction module 208 may extract an area to full recovery and peak amplitude from the skin conductance signal, an area to half recovery from the inter-heartbeat interval, a peak amplitude of the skin conductance, an average value of the skin conductance, the amplitude of the inter-beat interval signal.

The extracted features from the signal are then used to classify and diagnose the subject (step 308). In some implementations, two or more of the extracted features are processed by classification module 206 to determine if the subject 103 suffers from PTSD or another type of disorder. In some implementations, the method 300 also includes determining a threshold responsive to at least one of an age of the subject, an ethnic background of the subject, a sex of the subject, and a baseline response of the subject. In these implementations, the classification module 206 combines and applies weights to the processed extracted features and compares the combined value to the threshold. The weighted features can be combined simply by adding them together, multiplying them together, combining them according to a polynomial expression, or any other arithmetic process. In such implementations, the classifier identifies a subject 103 as having PTSD if the combined value exceeds the threshold, and not having PTSD if the combined value falls below the threshold. In other implementations, the diagnostic module 106 returns a likelihood value corresponding to a determined likelihood that the subject has PTSD. In some implementations, the method also includes displaying the results of the classification to a clinician, care provider, and/or to the subject by outputting the results via a display device coupled to the display driver.

The invention may be embodied in other specific forms without departing from the spirit or essential characteristics thereof. The forgoing implementations are therefore to be considered in all respects illustrative, rather than limiting of the invention.

What is claimed is:

1. A method for detecting a stress disorder:
   exposing a subject to a stimulus;
   collecting, with a plurality of sensors, a plurality of physiological signals during the subject's exposure to the stimuli, the plurality of physiological signals comprising at least an interbeat interval signal and a skin conductance signal;
   extracting a feature from each of the plurality of physiological signals; and
   classifying the subject into one of a first category indicating the subject is suffering from post-traumatic stress disorder, a second category indicating the subject is not suffering from post-traumatic stress disorder, or a third category indicating the subject was exposed to a traumatic event but does not suffer from post-traumatic stress disorder based on a function of the extracted features.

2. The method of claim 1, wherein the extracted features includes at least one of an area under one of the plurality of physiological signals from exposure to the stimuli to full recovery feature, an area under one of the plurality of physiological signals from exposure to the stimuli to half recovery feature, a peak amplitude feature, a standard deviation feature, a rise time from a first low point feature, a rise time from a response onset feature, a rise rate from a first low point feature, a time to full recovery from exposure to the stimuli, a latency time, and an average value feature.

3. The method of claim 1, wherein the stimuli comprise at least one of audio stimuli and visual stimuli.

4. The method of claim 3, further comprising presenting the visual stimuli to the subject via a virtual reality display device.

5. The method of claim 1, further comprising selecting the stimuli based on a traumatic event previously experienced by the subject.

6. The method of claim 1, wherein classifying the subject comprises:
applying weights to the extracted features,
combining the weighted features; and
comparing the combined weighted features to a threshold.

7. The method of claim 6, wherein the threshold is selected responsive to at least one of an age of the subject, an ethnic background of the subject, a sex of the subject, and a baseline response of the subject.

8. The method of claim 1, further comprising classifying the subject as suffering from post-traumatic stress disorder with one of a neural network, a Bayesian network, a linear discriminant classifier, or a support vector machine.

9. The method of claim 1, wherein the plurality of physiological signals further comprise at least one of a respiratory rate signal, a finger pulse amplitude signal, an electrocardiographic signal, a skin conductance signal, and an electroencephalographic signal.

10. A system for detecting stress disorder, comprising:
an analog to digital converter (ADC), the ADC configured to record a plurality of physiological signals during a subject's exposure to a stimuli, the plurality of physiological signals comprising at least an interbeat interval signal and a skin conductance signal;
a feature extraction module configured to extract a feature from each of the plurality of physiological signals; and
a classification module configured to classify the subject into one of a first category indicating the subject is suffering from post-traumatic stress disorder, a second category indicating the subject is not suffering from post-traumatic stress disorder, or a third category indicating the subject was exposed to a traumatic event but does not suffer from post-traumatic stress disorder based on a function of the extracted features.

11. The system of claim 10, further comprising a stimulus delivery system.

12. The system of claim 11, wherein the stimulus delivery system is configured to expose the subject to the plurality of audio and/or visual stimuli.

13. The system of claim 11, wherein the stimulus delivery system comprises a virtual reality display.

14. The system of claim 11, wherein the stimulus delivery system is configured to select the stimuli based on a traumatic experience previously experienced by the subject.

15. The system of claim 10, wherein the classification module is configured to classify the subject using at least one of a neural network, a Bayesian network, a linear discriminant classifier, or a support vector machine.

16. The system of claim 12, wherein the processor is configured to classify the subject by applying weights to the extracted features, combining the weighted features, and comparing the combined weighted features to a threshold.

17. The system of claim 16, wherein the threshold is selected responsive to at least one of an age of the subject, an ethnic background of the subject, a sex of the subject, and a baseline response of the subject.

18. The system of claim 10, wherein the extracted physiological features includes at least one of an area under one of the plurality of physiological signals from exposure to the stimuli to full recovery feature, an area under one of the plurality of physiological signals from exposure to the stimuli to half recovery feature, a peak amplitude feature, a standard deviation feature, a rise time from a first low point feature, a rise time from a response onset feature, a rise rate from a first low point feature, and an average value feature.

* * * * *